(12) United States Patent
Martin et al.

(10) Patent No.: US 6,812,704 B2
(45) Date of Patent: Nov. 2, 2004

(54) DEVICE FOR EVALUATING THE DENSITY OF PROTONS PRESENT IN A GIVEN BODY USING NMR

(75) Inventors: Jean-Pierre Martin, Le Vaudreuil (FR); Marcel Locatelli, Montbonnot (FR)

(73) Assignee: Innov.Pro, Le Vaudreuil (FR)

( * ) Notice: Subject to any disclaimer, the term of this patent is extended or adjusted under 35 U.S.C. 154(b) by 0 days.

(21) Appl. No.: 10/332,137

(22) PCT Filed: Jul. 10, 2001

(86) PCT No.: PCT/FR01/02211
§ 371 (c)(1),
(2), (4) Date: Jan. 6, 2003

(87) PCT Pub. No.: WO02/06846
PCT Pub. Date: Jan. 24, 2002

(65) Prior Publication Data
US 2003/0184295 A1 Oct. 2, 2003

(30) Foreign Application Priority Data
Jul. 13, 2000 (FR) .............................. 00 09155

(51) Int. Cl.[7] .................................. G01V 3/00
(52) U.S. Cl. .................................... 324/318
(58) Field of Search ................. 324/318, 303, 324/309, 306, 300, 307; 335/296–306

(56) References Cited

U.S. PATENT DOCUMENTS

| | | | | |
|---|---|---|---|---|
| 3,966,973 A | * | 6/1976 | Henry et al. | 324/307 |
| 4,717,876 A | * | 1/1988 | Masi et al. | 324/303 |
| 5,572,132 A | | 11/1996 | Pulyer et al. | 324/318 |
| 5,610,522 A | | 3/1997 | Locatelli et al. | 324/319 |
| 5,831,433 A | * | 11/1998 | Sezginer et al. | 324/303 |
| 6,114,851 A | * | 9/2000 | Kruspe et al. | 324/303 |
| 6,133,734 A | * | 10/2000 | McKeon | 324/303 |
| 6,459,262 B1 | * | 10/2002 | Wisler et al. | 324/303 |
| 6,493,572 B1 | * | 12/2002 | Su et al. | 324/318 |

* cited by examiner

Primary Examiner—Christopher W. Fulton
(74) Attorney, Agent, or Firm—Sughrue Mion, PLLC

(57) ABSTRACT

A device for evaluating the density of protons present in a given body with the possibility of identifying the material forming part of the constitution of the body and to which the protons belong. The device includes a permanent magnet having north and south poles, the magnet presenting a longitudinal axis of symmetry and a plane of symmetry perpendicular to the axis; two coils disposed at opposite ends of the magnet, centered on the axis, and symmetrical about the plane; a radio frequency electricity generator connected to the two coils in such a manner that the radio frequency electric current feeds the two cols so that the faces of the two coils respectively facing the two poles of the permanent magnet are of the same magnetic kind; and a receiver connected to the two cols to analyze the electrical signals delivered at the output of the two coils when the generator is disconnected from the two coils.

11 Claims, 3 Drawing Sheets

DEVICE FOR EVALUATING THE DENSITY OF PROTONS PRESENT IN A GIVEN BODY USING NMR

Figure 1:
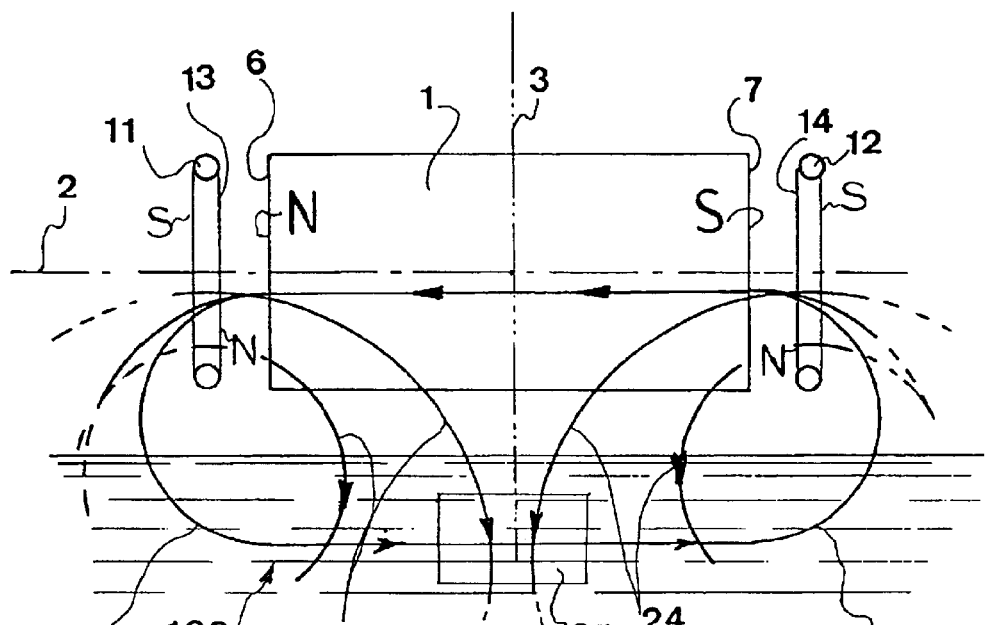

The present invention relates to devices for evaluating the density of protons present in a given body, making it possible to identify the material forming part of the constitution of said body and to which the protons belong, which devices find particularly advantageous applications in particular in the field of the food industry in order to determine the quantity of water and/or fat in foodstuffs, and in the field of the oil industry in order to determine, for example, the quantity of water in the rock surrounding the wall of a borehole, the distribution of pores within said rock, and/or its permeability.

There already exists a technique known as nuclear magnetic resonance (NMR) for determining the quantity of protons in a given material, i.e. the number of hydrogen free radicals, and possibly also for identifying said material. Numerous devices have been made for implementing that technique. Very briefly, those devices comprise means for inducing a static magnetic field in a given zone of the material to be investigated, with the lines of force of the field having a given direction for polarizing the protons present in said zone. Such means are generally constituted by a permanent magnet.

The device also comprises a transmitter antenna constituted for example by a magnetic coil powered by a radio frequency electricity generator, the coil being associated with the permanent magnet in such a manner that the lines of force of the radio frequency magnetic field induced in said zone by said coil when powered by radio frequency electrical current make a non-zero angle with the lines of force of the static field, and advantageously make an angle equal to ninety degrees.

The frequency of the radio frequency field is such that it corresponds to the precession frequency of protons in the static field so as to induce resonant interaction between the protons and the radio frequency field. This interaction makes it possible by means of the radio frequency field pulses to turn the polarization of the protons through an angle that depends on the amplitude of the radio frequency field and on the duration of the pulses.

The device also comprises a receiver antenna constituted for example by a magnetic coil which may be constituted by the same coil as the transmitter coil, the receiver coil picking up the magnetic field produced by the protons once the radio frequency current has been switched off and while the protons are returning to their initial polarization under the sole action of the static field of the permanent magnet.

The amplitude of the magnetic field detected by the receiver antenna is a function of the number of protons that have been excited in the investigation zone, and the time taken by the protons to switch from their second polarization back to the first, known in the art as the "relaxation time", is an image of the nature of the substances to which the protons belong.

That technique is well known to the person skilled in the art and is described in numerous documents, so it is not described in greater detail herein.

There exist numerous devices enabling that technique to be implemented, and that satisfy the above description, for example the device described in U.S. Pat. No. 5,610,522.

Nevertheless, all presently-known devices of that type either present a structure that is very complex, or else they lack power, or else they cannot be applied to fields that are as different as the food industry and the oil industry.

An object of the present invention is thus to provide a device for evaluating the density of protons in a material contained in a given body, with the possibility of identifying said material, which device mitigates to a considerable extent the drawbacks of prior art devices and can be applied to fields that are as different as the food industry and the oil industry.

More precisely, the present invention provides a device for evaluating the density of protons present in a given body with the possibility of identifying the material forming part of the constitution of the body and to which the protons belong, the device being characterized by the fact that it comprises:

a permanent magnet having two poles, respectively a north pole and a south pole, said permanent magnet presenting a longitudinal axis of symmetry oriented north-south and a plane of symmetry perpendicular to said longitudinal axis of symmetry;

at least first and second cylindrical coils disposed at opposite ends of the permanent magnet, substantially centered on said longitudinal axis of symmetry, and substantially symmetrical about said plane of symmetry;

a controllable radio frequency electricity generator having outputs respectively connected to the first and second coils so that the two coils are fed at radio frequency so that the faces of the two coils respectively facing the two poles of the permanent magnet are of the same magnetic kind; and a receiver having inputs respectively connected to said two coils, said receiver being suitable for analyzing the electrical signals delivered at the output of the two coils when the generator is disconnected from said two coils.

Figure 2:
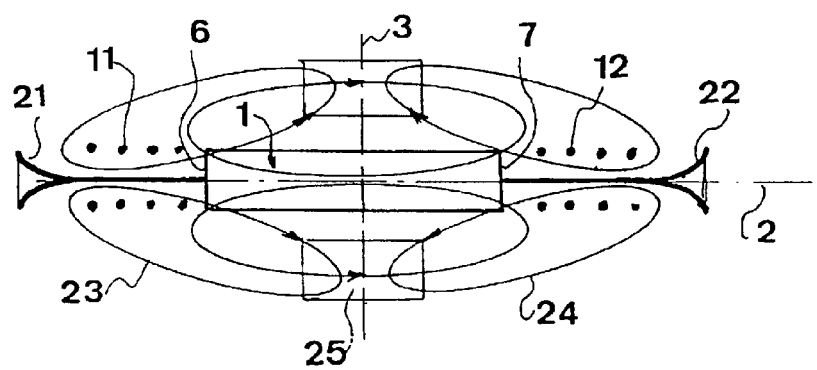
Figure 3:
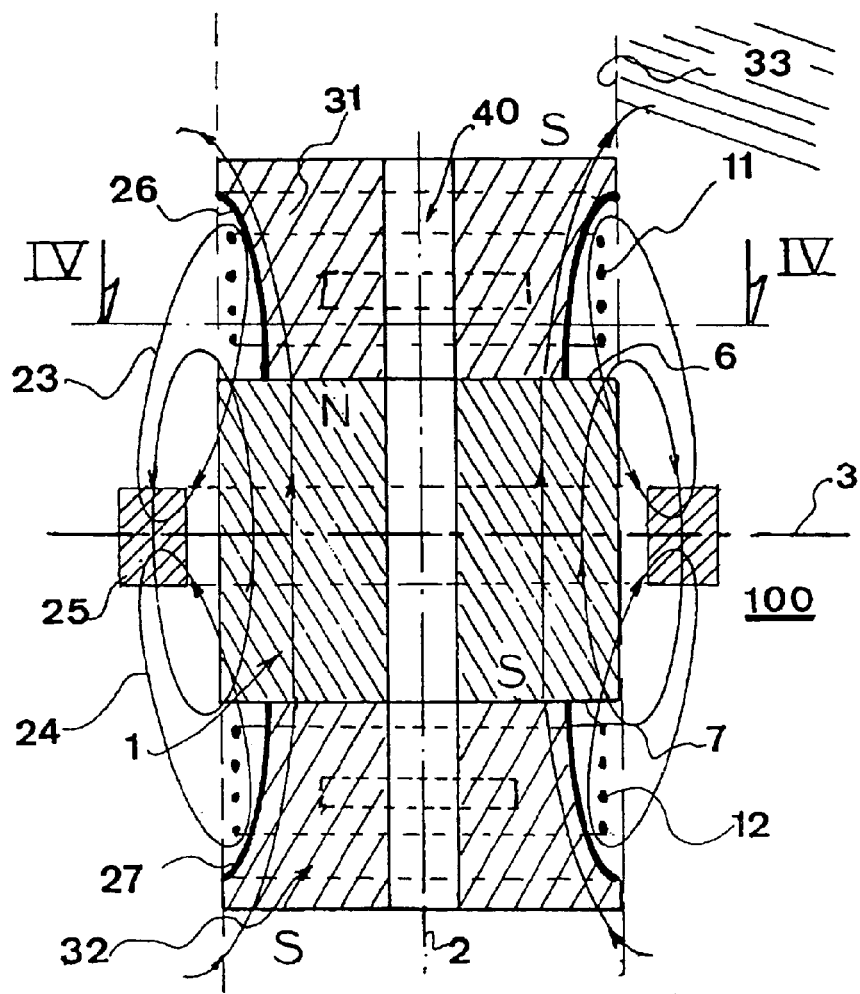
Figure 4:
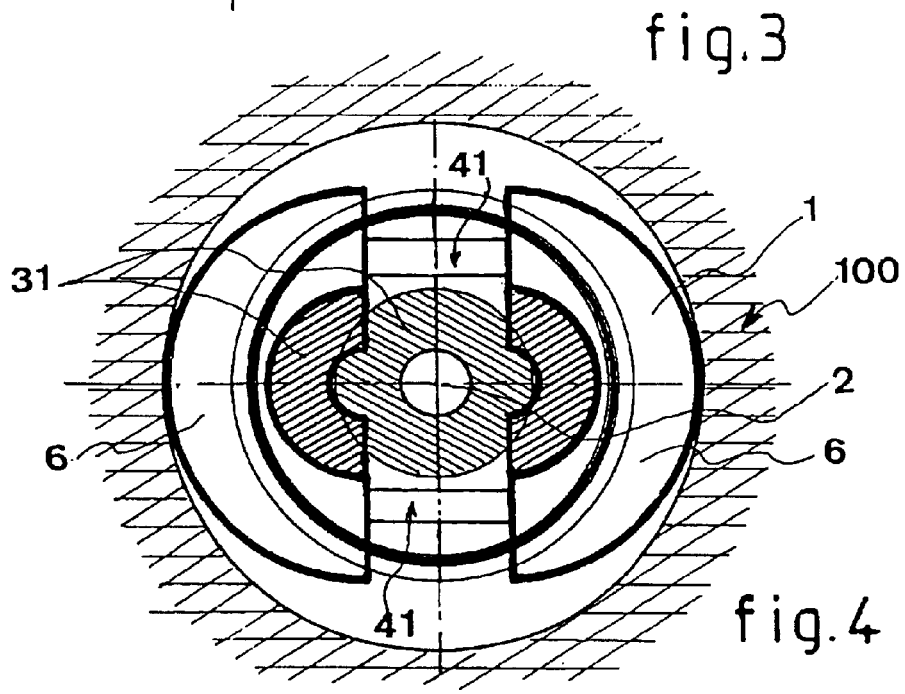
Figure 5:
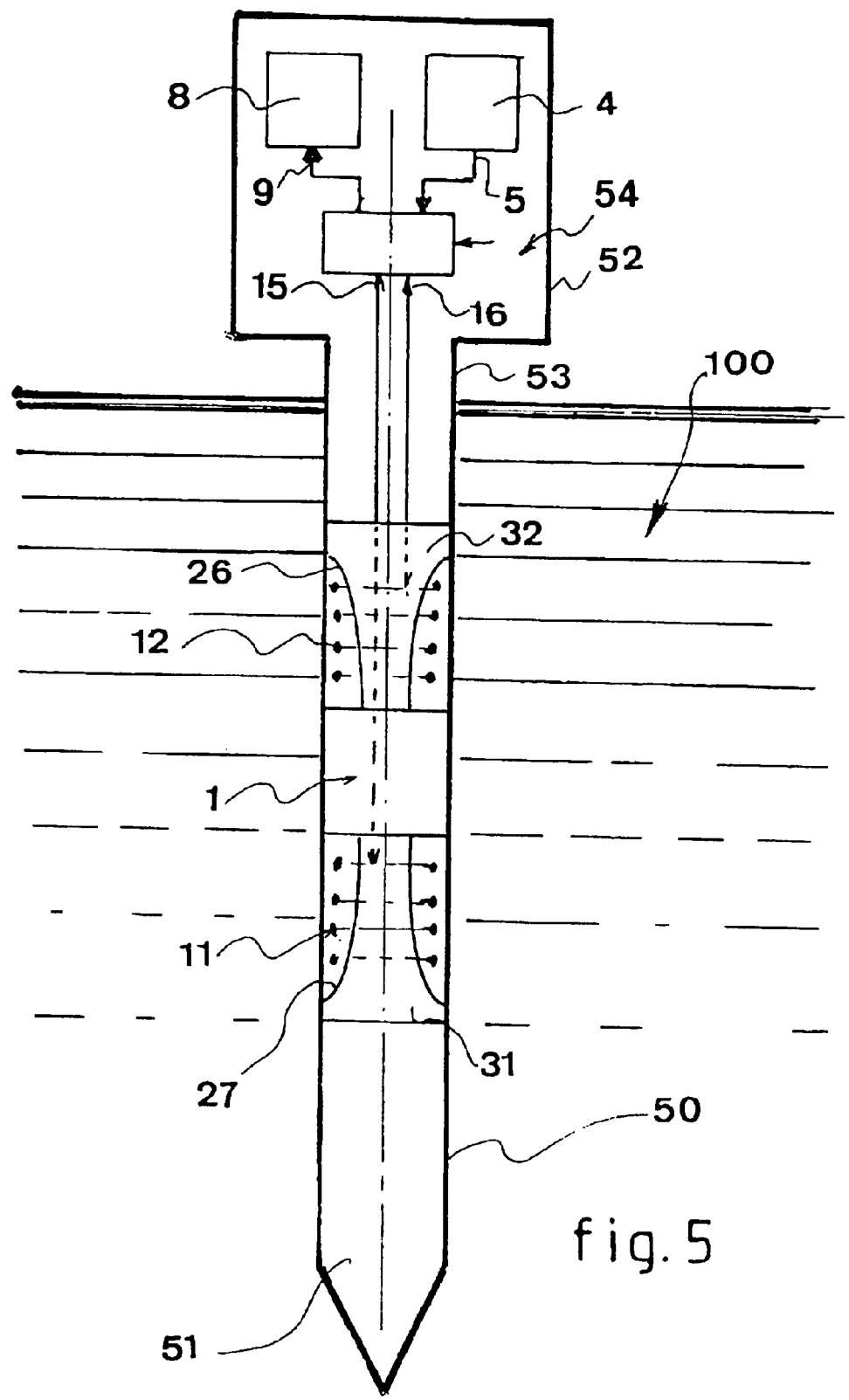

Other characteristics and advantages of the invention appear from the following description given with reference to the accompanying drawings by way of non-limiting illustration, in which:

FIG. 1 is a diagram showing a portion of a first embodiment of the device of the invention for evaluating the density of protons present in a given body with the possibility of identifying the material forming part of the constitution of said body and to which the protons belong;

FIGS. 2, 3, and 4 respectively show three other embodiments of the device of the invention constituting improvements of the embodiment shown in FIG. 1; and FIG. 5 shows an embodiment of the device of the invention in a particular application to the food industry.

It is specified that the five figures show different embodiments of the device of the invention for evaluating the density of protons present in a given body with the possibility of identifying the material forming part of the constitution of said body and to which the protons belong. Nevertheless, the same references are used therein regardless of the figure in which they appear and regardless of the way in which said elements are represented. Similarly, if elements are not specifically referenced in any one of the figures, their references can easily be found by referring to another figure.

It is also specified that when in the definition of the invention the subject matter of the invention is said to comprise "at least one" element having a given function, the embodiment described may have a plurality of such elements.

Similarly, if the embodiment of the invention as shown has a plurality of elements of identical function and if in the description it is not specified that the subject matter of the invention must necessarily have some particular number of those elements, then the subject matter of the invention may be defined as comprising "at least one" of those elements.

FIG. 1 is a diagram showing a portion of the device for evaluating the density of protons present in a given body 100 with the possibility of identifying the material forming part of the constitution of said body and having said protons belonging thereto, the other portion of the device being shown in FIG. 5.

With reference to FIGS. 1 and 5, the device comprises a permanent magnet 1 having two poles 6 and 7, respectively a north pole and a south pole, the permanent magnet presenting a longitudinal axis of symmetry 2 oriented in the north-south direction, and a plane of symmetry 3 perpendicular to said longitudinal axis of symmetry. Naturally, the permanent magnet 1 is advantageously in the form of a circular cylinder.

The device also comprises at least first and second cylindrical coils 11 and 12 disposed at opposite ends of the permanent magnet 1, being substantially centered on the longitudinal axis of symmetry 2 and being substantially symmetrical about the plane of symmetry 3. These coils 11 and 12 as shown in FIG. 1 are of the "flat" coil type, but they could be of any type, for example they could be solenoids as shown in FIG. 5.

With reference to FIG. 5, the device further comprises a controllable radio frequency electricity generator 4 having outputs 5 connected to the first and second coils 11 and 12 respectively so that the radio frequency feed to the two coils is such that the faces 13 and 14 of the two coils respectively facing the two poles 6, 7 of the permanent magnet 1 are of the same magnetic kind, and the device further comprises a receiver 8 having inputs 9 connected respectively to the two coils 11 and 12, the receiver being suitable for analyzing the electrical signals delivered at the outputs 15, 16 of the two coils when the generator is disconnected from the two coils.

Such an assembly having a generator 4 and a receiver 8 is well known in itself in the field of NMR as explained in the introduction to the present description. It is described in numerous prior documents and in order to simplify the present description it is therefore not described in greater detail herein.

In FIG. 1, the two coils 11 and 12 placed at opposite ends of the permanent magnet 1 are illustrated having their respective north faces (N) 13 and 14 facing the north and south faces (N and S) 6 and 7 of the permanent magnet so as to generate magnetic force lines 23, 24 oriented as shown in FIG. 1.

Nevertheless, the coils could be fed in the opposite manner so that it is their south faces (S) which face the north and south poles of the magnet. Under such circumstances, the magnetic force lines 23, 24 would have the same shape as those shown in FIG. 1, but would be oriented in the direction opposite to that shown in the figure.

Such a device operates on the NMR principle. This operation is well known, but it is nevertheless outlined briefly below.

When it is desired to measure the density of protons in the body 100, the device is brought as close as possible to the body, while the generator 4 and the receiver 8 are deactivated. Under the effect of the permanent static magnetic field, the protons become oriented in the zone 25 which is in the form of an annular toroidal zone substantially centered on the axis of symmetry 2 and on the plane of symmetry 3, and relatively close to the side wall of the permanent magnet 1, following the lines of force 29 of said permanent field.

The generator 4 is then activated to feed the coils 11 and 12 with radio frequency electrical current. Each coil thus creates an induced magnetic field at radio frequency, having respective lines of force 23 and 24 which are perpendicular to the lines of force 29 in the above-defined zone 25. In addition, and as a consequence of the structural characteristics described above, the lines of force of the magnetic fields induced by the two coils in said zone 25 are oriented in the same direction which has the effect of creating a total radio frequency magnetic field of relatively large intensity.

Under the action of this induced magnetic field, the polarization direction of the protons is controlled because of the resonant interaction, and the angle of rotation is a function of the amplitude of the radio frequency pulse and of its duration, and said angle can advantageously be ninety degrees. By way of example, the radio frequency signal transmitted by the generator 4 is at about 4 megahertz, and the coils are designed so as to create an induced magnetic field of Tesla order.

The generator 4 is then deactivated and the receiver 8 is activated to pick up the signals delivered at the output from the coils as created by the magnetic field produced by the protons returning from their second polarization to the first. Analysis of the signal picked up by the receiver 8 makes it possible, as a function of signal amplitude, to determine proton density, and as a function of the way the signal varies over time, possibly also to identify the nature of the substance containing the protons.

Nevertheless, in order to increase the intensity of the magnetic field induced by the coils essentially in the zone 25, as shown diagrammatically in FIG. 2, it is advantageous for the device further to comprise first and second magnetic reflectors 21 and 22 mounted to co-operate respectively with the first and second coils 11 and 12 so as to concentrate the magnetic flux 23, 24 that is created by each magnetic coil 11, 12 in the above-defined zone 25.

In an advantageous embodiment, the two magnetic reflectors 21 and 22 are constituted by two concave or similarly-shaped surfaces of revolution 26, 27 about the axis of symmetry 2 and they are associated with the two coils 11 and 12 respectively in such a manner that their centers of curvature are situated in the vicinity of the plane of symmetry 3, each concave surface of revolution being constituted by a layer of an electrically-conductive material such as copper, gold, etc., for example.

In order also to obtain a maximum amount of static magnetic flux induced by the permanent magnet 1, essentially in the zone 25, the device advantageously further comprises two symmetrical pole pieces 31 and 32 mounted as shown in FIG. 3 to co-operate with the two poles 6 and 7 of the permanent magnet, these two pole pieces being rotated inside respective ones of the two coils 11 and 12 and being arranged to concentrate the lines of force of the static magnetic field generated by the permanent magnet 1 substantially in the zone 25. These two pole pieces 31 and 32 are made of a material such as iron, soft ferrite, etc., for example.

When the device has these two pole pieces, it is advantageous for the two concave surfaces of revolution 26 and 27 to be made, as shown in FIG. 3, on the outer side surfaces of the two pole pieces, the above-defined layer of electrically-conductive material being deposited directly on the outer side surface of each pole piece 31, 32.

Given that in its most advantageous applications, such a device is intended to be inserted in holes, boreholes, etc., it is advantageous for its maximum outside dimensions taken in planes parallel to the plane of symmetry 3 of the two coils 11, 12, of the two concave surfaces of revolution 26, 27, and of the two pole pieces 31, 32 respectively, to be no greater than the maximum outside dimension of the permanent magnet 1 in a plane parallel to the plane of symmetry 3, as shown diagrammatically in FIG. 3.

In particular, when such a device is for penetrating in a borehole 33 and its cross-section, i.e. essentially the cross-section of its permanent magnet 1, is substantially equal to that of the borehole, in order to enable the device to travel easily along the borehole without being subjected to a piston effect, it is advantageous for the device further to include a continuous through hole 40 extending substantially along the axis of symmetry 2 through the permanent magnet 1 and the two pole pieces 31 and 32, as shown in FIG. 3.

This through hole 40 allows the atmosphere contained in the borehole to pass through the device as it moves along the borehole. Advantageously, it can also pass various tools, such as sondes, cables, rods, of the types commonly used in the oil industry, in particular.

The device may also be needed for use in boreholes of different sections. Thus, in an advantageous embodiment, as shown in FIG. 4, the permanent magnet 1 and the pole pieces 31 and 32 are respectively made up of at least two portions suitable for being associated on a plane containing the axis of symmetry 2 so as to form the permanent magnet and the pole pieces, in which case the device has means 41 for causing the two portions to move in directions perpendicular to the axis of symmetry, e.g. electrical actuators or the like.

In this configuration, it is possible to keep the coils 11, 12 in their initial shape, with the displacement of the two portions being restricted to the space between the pole pieces and the coils. Nevertheless, with flat or similar coils, it is possible to increase the displacement of the two portions by making the coils as open loops of an electrically-conductive wire that is elastic.

As mentioned above, the device of the invention has numerous applications. In particular it can be used to determine the quantity of water and/or fat contained in foodstuffs.

FIG. 5 shows an embodiment that is more particularly adapted to this application.

For this purpose, the device may advantageously further comprise a sheath 50 in the form of a needle suitable for penetrating into the body 100 via one of its ends 51, the assembly comprising the permanent magnet 1, the pole pieces 31, 32, and the concave surfaces of revolution 26, 27 being situated inside the sheath, e.g. being made of a non-magnetic and dielectric material, for example a plastics material, such as a material known under the trademark "Nylon", etc.

In order to facilitate handling, particularly in this application, the device further comprises a handle 52 secured to the end 53 of the sheath opposite from its ends 51 enabling the sheath to penetrate into the body 100. A housing 54 is made in the handle and it can receive the generator 4, the receiver 8, an electrical power supply, and all the usual peripherals that are well known for the purpose of making the device independent so that it can be used at any location and at any time.

What is claimed is:

1. A device for evaluating the density of protons present in a given body (100) with the possibility of identifying the material forming part of the constitution of the body and to which the protons belong, the device being characterized by the fact that it comprises:
   a permanent magnet (1) having two poles (6, 7), respectively a north pole and a south pole, said permanent magnet presenting a longitudinal axis of symmetry (2) oriented north-south and a plane of symmetry (3) perpendicular to said longitudinal axis of symmetry;
   at least first and second cylindrical coils (11, 12) disposed at opposite ends of the permanent magnet (1), substantially centered on said longitudinal axis of symmetry (2), and substantially symmetrical about said plane of symmetry (3);
   a controllable radio frequency electricity generator (4) having outputs (5) respectively connected to the first and second coils (11, 12) so that the two coils are fed at radio frequency so that the faces (13, 14) of the two coils (11, 12) respectively facing the two poles (6, 7) of the permanent magnet (1) are of the same magnetic kind; and
   a receiver (8) having inputs (9) respectively connected to said two coils (11, 12), said receiver being suitable for analyzing the electrical signals delivered at the output (15, 16) of the two coils when the generator is disconnected from said two coils.

2. A device according to claim 1, characterized by the fact that it further comprises first and second magnetic reflectors (21, 22) mounted to co-operate with the first and second coils (11, 12) respectively so as to concentrate the magnetic flux (23, 24) that can be created by each magnetic coil (11, 12) in a zone (25) that is substantially centered on said plane of symmetry (3) and that is close to said permanent magnet (1).

3. A device according to claim 2, characterized by the fact that the two magnetic reflectors (21, 22) are constituted by two concave surfaces of revolution (26, 27) about the axis of symmetry (2) and are associated respectively with said coils (11, 12) in such a manner that their centers of curvature are situated in the vicinity of the plane of symmetry (3), each of the two concave surfaces of revolution being constituted by a layer of electrically-conductive material.

4. A device according to any one of claims 1 to 3, characterized by the fact that it further comprises two symmetrical pole pieces (31, 32) mounted to co-operate with the two poles (6, 7) of the permanent magnet, said two pole pieces passing inside respective ones of said two coils (11, 12) and being arranged to concentrate the lines of force (29) of the magnetic field generated by said permanent magnet (1) substantially in said zone (25).

5. A device according to claim 4, characterized by the fact that the two concave surfaces of revolution (26, 27) are made on the outer side surfaces of the two pole pieces (31, 32).

6. A device according to claim 5, characterized by the fact that the maximum outside dimensions taken in planes parallel to the plane of symmetry, respectively of the two coils (11, 12), of the two concave surfaces of revolution (26, 27), and of the two pole pieces (31, 32) are no greater than the maximum overall dimension of the permanent magnet (1) taken in a plane parallel to said plane of symmetry (3).

7. A device according to claim 6, characterized by the fact that it has a continuous through hole (40) made substantially along the axis of symmetry (2) through the permanent magnet (1) and the two pole pieces (31, 32).

8. A device according to claim 7, characterized by the fact that said permanent magnet (1) and the pole pieces (31, 32) are constituted respectively as at least two portions suitable for being associated along a plane containing the axis of symmetry (2) to form said permanent magnet and said pole pieces, and that they have means (41) for controlling the displacement of said two portions in directions perpendicular to said axis of symmetry.

9. A device according to any one of claim 5, characterized by the fact that it further comprises a sheath (50) in the form of a needle suitable for penetrating in said body (100) via one of its ends (51), the assembly comprising the permanent magnet (1), the pole pieces (31, 32), and the concave surfaces of revolution (26, 27) being situated inside said sheath.

10. A device according to claim 9, characterized by the fact that said sheath is made of non-magnetic material.

11. A device according to claim 9, characterized by the fact that it further comprises a handle (52) secured to the end (53) of the sheath that is opposite from its end (51) whereby the sheath is suitable for penetrating into said body (100), a housing (54) being made in said handle, with the generator (4) and the receiver (8) being situated in said housing.

* * * * *